United States Patent [19]

Imai et al.

[11] Patent Number: 5,252,629
[45] Date of Patent: Oct. 12, 1993

[54] ADHESIVES FOR DENTIN

[75] Inventors: Yohji Imai, Chiba; Shigenobu Kusakai, Tokyo, both of Japan

[73] Assignee: GC Corporation, Tokyo, Japan

[21] Appl. No.: 870,594

[22] Filed: Apr. 17, 1992

[30] Foreign Application Priority Data

Jun. 19, 1991 [JP] Japan ................................ 3-173407

[51] Int. Cl.[5] ................................ C08K 3/10
[52] U.S. Cl. .................................... 523/118; 523/115; 523/116; 524/781; 524/785; 526/91; 526/204; 526/211
[58] Field of Search ................ 524/781, 785; 523/115, 523/116, 118; 526/91, 204, 211

[56] References Cited

U.S. PATENT DOCUMENTS 4,534,839  8/1985  Schaefer ..................... 204/159.23
4,593,054  6/1986  Asmussen et al. ................ 523/118
4,873,269  10/1989  Nakazato ...................... 523/115

FOREIGN PATENT DOCUMENTS 2193967  2/1988  United Kingdom .
2202543  9/1988  United Kingdom .

*Primary Examiner*—Paul R. Michl
*Assistant Examiner*—John J. Guarriello
*Attorney, Agent, or Firm*—Oblon, Spivak, McClelland, Maier & Neustadt

[57] ABSTRACT

An adhesive showing a strong bonding effect on dentin characterized by comprising in combination a primer comprising a water-miscible monomer and a salt of copper, iron or cobalt, and a curing composition comprising a methacrylate monomer and a polymerization initiator containing a (thio)barbituric acid derivative as one component.

6 Claims, No Drawings

ADHESIVES FOR DENTIN

BACKGROUND OF THE INVENTION

The present invention concerns an adhesive for dentine, and relates more particularly to an adhesive particularly efficacious for the dentin of a tooth, which makes use of a primer characterized by containing a metal salt.

In dental therapy, the bond strength of the body, especially, dentin of a tooth with respect to other materials such as polymers, metals or porcelains must be increased. To this end, various forms of adhesives have already been proposed in the art.

Such dental adhesives are represented by:

an adhesive composition comprising (1) a radically polymerizable methacrylate monomer, (2) a mixture of benzoyl peroxide and an aromatic tertiary amine with or without a sulfinic acid salt, which serves as a polymerization catalyst and (3) a filler, or an adhesive composition comprising (1) a radically polymerizable methacrylate monomer, (2) a photopolymerization initiator comprising camphor quinone serving as a photosensitizer and an amine acting as a reducing agent, such as N,N-dimethylaminoethyl methacrylate, and (3) a filler, and an adhesive composition comprising (1) a radically polymerizable methacrylate monomer, (2) 4-methacryloyloxyethoxycarbonyl phthalic anhydride (4-META) which serves as an adhesionaccelerating monomer, and (3) a partial oxide of tributyl borane (TBBO) acting as a polymerization catalyst and PMMA serving as a filler.

In conventional adhesive compositions known so far in the art, various compounds are used as the polymerization initiators for radically polymerizable monomers. However, no sufficient bond strength is obtained with the exception of the use of TBBO. In order to better adhesion, it has been put forth to use adhesion-promoting monomers or monomers showing an affinity for dentin, e.g., carboxyl group-containing monomers such as 4-methacryloyloxyethoxycarbonyl phthalic acid (4-MET) or its anhydride (4-META) and 10-methacryloyloxydecyl malonic acid (MAC-10) and phosphoric acid group-containing monomers such as 10-methacryloyloxydecyl dihydrogen phosphate, but none of them are well effective for dentin.

Among conventional adhesives, TBBO-based systems are excellent, but a problem associated with the system is that TBBO must be used in large amounts, say 10% or more relative to the monomer only to obtain slow curing. Another problem is that they are allowed to be used substantially with a methyl methacrylate monomer alone; that is, they cannot be used in combination with dimethacrylates. In addition, the pre-treatment of dentin presents a clumsy problem that enamel have to be pretreated with phosphoric acid and dentin have to be pretreated with a citric acid solution containing ferric chloride, respectively. In order to overcome such problems inherent in TBBO, it is required to elaborate different polymerization initiation system. Benzoyl peroxide/aromatic tertiary amine/sulfinic acid salt-based initiators are considered effective for bonding to a dentin, but such available methods as set forth in Japanese Patent publication Nos. 56-33363 and 59-15468 fail to provide a sufficient bond strength to a dentin.

Apart from what has been described, it has been found that (thio) barbituric acid derivative/copper salt/chlorine ion-based initiators are considerably effective for bonding to a dentin—see for instance "Dental Material And Equipment", Vol. 8, Special Edition No. 14, pp. 89–90 (1989). However, they offers the same clumsy problem as is with the case of TBBO. Nor is any sufficient bond strength obtained; there is left much to be desired in this regard.

SUMMARY OF THE INVENTION

According to this invention, a further increase in bond strength and a more simplified pre-treatment are now achieved by the use of a combination of a polymerization initiator containing this (thio)barbituric acid derivative as one component with a primer.

More specifically, this invention provides a solution to the above problems by coating onto a dentin a primer comprising the salts of copper, iron or cobalt and 2-hydroxyethyl methacrylate (HEMA) and applying onto the primer one of the following compositions for curing:

(1) a curing composition comprising a methacrylate monomer and a (thio) barbituric acid derivative/copper salt/chlorine ion-based initiator, (2) a curing composition comprising a methacrylate monomer and a camphor quinone/(thio)barbituric acid derivative/copper salt/chlorine ion-based initiator, and (3) a curing composition comprising a methacrylate monomer and a camphor quinone/(thio)barbituric acid derivative-based initiator.

DETAILED EXPLANATION OF THE INVENTION

Examples of the salts of copper, iron and cobalt added to the HEMA primer are chlorides, nitrates, sulfates, acetates, acrylates, methacrylates, salts of organic acids, organic complexes such as acetylacetone, and so on. These salts of polyvalent metal compounds may have any desired number of valency. Typical copper salts are exemplified by cupric chloride, copper nitrate, copper acetate, copper acrylate, copper methacrylate and acetylacetone copper.

The iron salts used, for instance, are ferric chloride, ferric nitrate, ferric sulfate, iron acrylate, iron methacrylate and acetylacetone iron, while the cobalt salts are typically cobalt (II) chloride, cobalt (II) nitrate, cobalt (II) acetate, cobalt acrylate, cobalt methacrylate and acetylacetone cobalt. As will be noted from the examples given later, the best results will be obtained, if the amount of the metal salt added to the primer lies in the range of 0.0005 to 0.05% by weight for the copper salt and 0.005 to 0.5% by weight for iron salt or cobalt salt, respectively.

The primer has an HEMA concentration lying in the range of 1~50%, preferably 5~40%, and may be used in the form of water or a mixed liquid of water and a water-miscible organic solvent such as ethanol, isopropanol, acetone and tetrahydrofuran. In addition to HEMA, this primer may contain a carboxyl or phosphoric group-containing radically polymerizable monomer in such an amount that it is dissolvable in the primer.

For the purpose of reinforcing a dentin, an additive such as sodium fluoride may be incorporated in the primer in such an amount that it is dissolvable in the primer.

In addition to HEMA, for instance, hydroxypropyl methacrylate, 2,3-dihydroxypropyl methacrylate and N-vinylpyrrolidone may be used as the water-miscible monomer to which the metal salt is added, and HEMA may be partly or wholly substituted by them. The primer may be either a one-pack or a two-pack type of liquid formulation which may be used in combination.

The (thio)barbituric acid derivative used for initiating polymerization, for instance, may be 1,3,5-trimethyl, 1,3,5-triethyl, 1,3-dimethyl-5-ethyl, 1,5-dimethyl, 1-methyl-5-ethyl, 1-methyl-5-propyl, 5-ethyl, 5-propyl, 5-butyl, 1-benzyl-5-phenyl, 1-cyclohexyl-5-ethyl (thio)-barbituric acids.

The chlorine ion source used, for instance, may be such hydrochlorides of metals as cupric chloride, ferric chloride and cobalt (II) chloride as well as hydrochlorides of triethyl-amine, propylamine and butylamine and such quaternary ammonium salts as methacryloylcholine chloride and triethylbenzylammonium chloride. Such polymerization initiators may be used with a peroxide such as benzoyl peroxide and/or a sulfinic acid salt such as sodium toluenesulfinic acid or may be used in combination.

According to this invention, the primer is coated onto the surface of a tooth, followed by drying, and then provided thereon with one of (1) a curing composition comprising a methacrylate monomer and a (thio) barbituric acid derivative/copper salt/chlorine ion-based initiator, (2) a curing composition comprising a methacrylate monomer and a camphor quinone/(thio)barbituric acid derivative/copper salt/chlorine ion-based initiator, and (3) a curing composition comprising a methacrylate monomer and a camphor quinone/(thio)barbituric acid derivative-based initiator. However, it is noted that the composition used is not critical, if it is effectively cured by one of these initiators. The curing composition may be a resin in itself, or a bonding agent for composite resin or an adhesive serving as a liner. Thus, this invention is not limited to the examples given later.

As already noted, a dentin may be pre-treated for bonding with an aqueous solution of phosphoric acid, citric acid, ethylenediamine tetra-acetate or citric acid containing cupric or ferric chloride, but in view of concurrent treatment of and adhesive properties to enamel, preference is given to using a 5~40% aqueous solution of phosphoric acid.

This invention will now be explained more specifically but not exclusively with reference to the following examples.

Prior to giving examples, how to measure bond strength will now be explained.

(1) A bovine anteriortooth was cut on its labial side to expose the dentin surface to open view, and then polished by No. 600 emery paper to prepare a testing surface. After treated with an aqueous solution of phosphoric acid for 30 seconds, washed with water and dried, that surface was applied thereon with an adhesive plastic tape having thereon a pore of 5 mm in diameter to define the coverage. The primer of this invention was then coated onto the testing surface, followed by drying. Subsequently placed on the primer was a paste obtained by mixing a liquid component containing methyl methacrylate (MMA) with 5% of 2-hydroxyethyl methacrylate and 0.003% of cupric chloride with a powder component containing polymethyl methacrylate (PMMA) powders with 2% of a (thio) barbituric acid derivative at a 1:1 ratio for bonding an acrylic rod onto it. The sample was allowed to stand at room temperature for 30 minutes, the immersed in distilled water of 37° C. for a further 24 hours, and finally subjected to tensile testing to measure the bond strength.

(2) After the primer had been coated onto the testing surface following the procedure of (1), prepared were a liquid A consisting of a methacrylate monomer/a copper salt/chlorine ions and a liquid B consisting of a (thio) barbituric acid derivative/ethanol. These liquids were mixed together at a 1:1 ratio to prepare a bonding agent, which was in turn coated onto the primer. After the volatile components had been evaporated off at a low air pressure, a 1 mm thick silicone rubber spacer having pores of 6 mm in diameter was placed on the bonding agent, which pores were then filled with a composite resin "Microrest AP" for curing. The spacer was removed, followed by bonding an acrylic rod onto the bonding agent with the use of an instantaneously polymerizing resin. The sample was dipped in distilled water of 37° C. for 24 hours and then subjected to tensile testing to measure the bond strength.

(3) After the primer had been applied onto the testing surface following the procedure of (1), prepared were a liquid A consisting of a methacrylate monomer/a copper salt/chlorine ions/camphor quinone and a liquid B consisting of a (thio) barbituric acid derivative/ethanol. The liquids were mixed together at a 1:1 ratio to prepare a bonding agent, which was in turn applied onto the primer, followed by evaporation of the volatile components at a low air pressure. After that, the bonding agent was irradiated with light with a light irradiator GC Light VL-1 (made by GC Corporation) for 30 seconds. A 1 mm thick silicone rubber spacer having 6 mm diameter pores was placed on the bonding agent, followed by filling the pores with a composite resin Graft LC. Curing then took place by 60 second irradiation with light, followed by the procedures of (2).

(4) The procedures of (3) were followed with the exception that a liquid A consisting of a methacrylate monomer/camphor quinone and a liquid B consisting of a (thio) barbituric acid derivative/ethanol were prepared and mixed together at a 1:1 ratio to give a bonding agent.

EXAMPLE 1

A primer consisting of 0.003 g of cupric chloride, 35 g of 2-hydroxyethyl methacrylate (HEMA) and 65 g of water was coated onto a dentin which had been treated with a 10% aqueous solution of phosphoric acid, and tensile testing was done with 5-butyl barbituric acid according to the procedures explained in (1). A bond strength of 14.0 MPa was obtained.

EXAMPLE 2

The procedure of Example 1 was followed with the exception that a dentin was treated with a 40%, not 10%, aqueous solution of phosphoric acid. A bond strength of 13.2 MPa was obtained.

COMPARATIVE EXAMPLE 1

The procedure of Example 1 was followed with the exception that a dentin was treated with a 10% aqueous solution of phosphoric acid but not coated with any primer. A bond strength of 4.5 MPa was obtained.

COMPARATIVE EXAMPLE 2

The procedure of Example 1 was followed with the exception that a dentin was treated with a 40% aqueous solution of phosphoric acid but not coated with any primer. A bond strength of 1.6 MPa was obtained.

COMPARATIVE EXAMPLE 3

The procedure of Example 1 was followed with the exception that a dentin was treated with a 10% aqueous solution of phosphoric acid and a primer of Example 1 from which cupric chloride was removed was used. A bond strength of 5.8 MPa was obtained.

EXAMPLE 3

The procedure of Example 1 was followed with the exception that a dentin was treated with a 10% aqueous solution of phosphoric acid and a primer of Example 1 containing 0.1 g of cupric chloride was used. A bond strength of 6.1 MPa was obtained.

EXAMPLE 4

The procedure of Example 1 was followed with the exception that a dentin was treated with a 10% aqueous solution of phosphoric acid and a primer consisting of 0.003 g of cupric chloride and 100 g of HEMA was used. A bond strength of 8.0 MPa was obtained.

EXAMPLE 5

The procedure of Example 1 was followed with the exception that dentin was treated with a 10% aqueous solution of phosphoric acid and a primer consisting of 0.003 g of cupric chloride, 65 g of HEMA and 35 g of water was used. A bond strength of 10.6 MPa was obtained.

EXAMPLE 6

The procedure of Example 1 was followed with the exception that a dentin was treated with a 40% aqueous solution of phosphoric acid and a primer consisting of 0.07 g of ferric chloride, 35 g of HEMA and 65 g of water was used. A bond strength of 13.5 MPa was obtained.

EXAMPLE 7

The procedure of Example 1 was followed with the exception that a dentin was treated with a 40% aqueous solution of phosphoric acid and a primer consisting of 1 g of ferric chloride, 35 g of HEMA and 65 g of water was used. A bond strength of 7.3 MPa was obtained.

EXAMPLE 8

The procedure of Example 1 was followed with the exception that dentin was treated with a 10% aqueous solution of phosphoric acid and a primer consisting of 0.01 g of ferric chloride, 35 g of HEMA and 65 g of water was used. A bond strength of 12.8 MPa was obtained.

EXAMPLE 9

The procedure of Example 1 was followed with the exception that a dentin was treated with a 10% aqueous solution of phosphoric acid and a primer consisting of 1 g of ferric chloride, 35 g of HEMA and 65 g of water was used. A bond strength of 6.8 MPa was obtained.

EXAMPLE 10

A primer consisting of 0.003 g of cupric chloride, 35 g of HEMA and 65 g of water was coated onto a dentin which had been treated with a 10% aqueous solution of phosphoric acid. Tensile testing was done with a liquid A consisting of 50 g of bis-GMA, 10 g of triethylene glycol dimethacrylate (3G), 40 g of HEMA and 0.003 g of cupric chloride and a liquid B consisting 2 g of 5-butyl barbituric acid and 98 g of ethanol according to the procedures (2) for bond strength. A bond strength of 9.0 MPa was obtained.

COMPARATIVE EXAMPLE 4

The procedure of Example 10 was followed with the exception that a dentin was treated with a 10% aqueous solution of phosphoric acid but not coated with any primer. A bond strength of 2.5 MPa was obtained.

COMPARATIVE EXAMPLE 5

The procedure of Example 10 was followed with the exception that a dentin was treated with a 10% aqueous solution of phosphoric acid and a primer of Example 10 from which cupric chloride was removed was used. A bond strength of 3.5 MPa was obtained.

EXAMPLE 11

A primer consisting of 0.003 g of copper methacrylate, 0.02 g of methacryloylcholine chloride, 35 g of HEMA and 65 g of water was coated onto a dentin which had been treated with a 10% aqueous solution of phosphoric acid. Tensile testing was done with a liquid A of Example 10 further containing 1 g of camphor quinone and a liquid B consisting 1 g of 1,3,5-trimethyl barbituric acid and 99 g of ethanol according to the procedures (3) for bond strength. A bond strength of 8.8 MPa was obtained.

COMPARATIVE EXAMPLE 6

Similar tensile testing was done with a primer of Example 11, from which copper methacrylate was removed. A bond strength of 4.0 MPa was obtained.

EXAMPLE 12

A primer consisting of 0.003 g of cupric chloride, 35 g of HEMA and 65 g of water was coated onto a dentin which had been treated with a 5% aqueous solution of phosphoric acid. Tensile testing was done with a liquid A consisting of 99 g of 3G and 1 g of camphor quinone and a liquid B consisting 1 g of 1,3,5-trimethyl barbituric acid and 99 g of ethanol according to Procedure (4) for bond strength. A bond strength of 8.5 MPa was obtained.

COMPARATIVE EXAMPLE 7

Similar tensile testing was done with a primer of Example 12, from which cupric chloride was removed. A bond strength of 5.7 MPa was obtained.

EXAMPLE 13

A primer consisting of 0.003 g of cupric chloride, 35 g of HEMA and 65 g of water was coated onto a dentin which has been treated with a 5% aqueous solution of phosphoric acid. Tensile testing was done with a liquid A consisting of 99 g of 3 G, 3 g of bis(2-methacryloyloxyethyl)phosphoric acid and 1 g of camphor quinone and a liquid B consisting 1 g of 1,3,5-trimethyl barbituric acid and 99 g of ethanol according to Procedure (4) for bond strength. A bond strength of 8.3 MPa was obtained.

EXAMPLE 14

The procedures of Example 1 were followed with the exception that a dentin was treated with a 10% aqueous solution of citric acid for 60 seconds. A bond strength of 13.5 MPa was obtained.

COMPARATIVE EXAMPLE 8

Similar testing was done following Example 14 without using any primer. A bond strength of 4.0 MPa was obtained.

EXAMPLE 15

The procedures of Example 1 were followed with the exception that a dentin was treated with a 15% aqueous solution of EDTA acid for 60 seconds. A bond strength of 13.2 MPa was obtained.

COMPARATIVE EXAMPLE 9

Similar testing was done following Example 15 without using any primer. A bond strength of 4.0 MPa was obtained.

EXAMPLE 16

A primer consisting of 0.003 g of cupric chloride, 30 g of 2-hydroxyethyl methacrylate (HEMA), 30 g of ethanol and 40 g of water was coated onto a dentin which had been treated with a 10% aqueous solution of phosphoric acid for similar testing according to Example 1. A bond strength of 14.5 MPa was obtained.

EXAMPLE 17

A primer consisting of 0.003 g of cupric chloride, 30 g of 2-hydroxyethyl methacrylate (HEMA), 0.01 g of sodium fluoride and 70 g of water was coated onto a dentin which had been treated with a 10% aqueous solution of phosphoric acid for similar testing according to Example 1. A bond strength of 13.0 MPa was obtained.

As the metal salt contained in the primer is entrained in an acid-treated dentin and the (thio)barbituric acid derivative in the curing composition is diffused in there, they form a redox system to generate radicals, thereby allowing the polymerization of HEMA and the monomer in the curing composition to begin and proceed rapidly. Thus, the polymerization and curing proceed from the surface of dentin, achieving strong adhesion.

What is claimed is:

1. An adhesive for dentin, prepared by a process comprising:
   (A) coating a surface with a primer comprising (i) a water-miscible monomer selected from the group consisting of 2-hydroxyethyl methacrylate, hydroxypropyl methacrylate, 2,3-dihydroxypropyl methacrylate, N-vinyl pyrrolidone and mixtures thereof, (ii) a metal salt selected from chlorides, nitrates, sulfates, acetates, acrylates, methacrylates or acetylacetonates of copper, iron or cobalt, wherein said salt of copper is present in an amount of from 0.0005 to 0.05% by weight of said primer, and said salt of iron or cobalt is present in an amount of from 0.005 to 0.5% by weight of said primer; and
   (B) applying a curing composition to said surface coated with said primer, said curing composition comprising (i) a methacrylate monomer, (ii) (thio)barbituric acid, which may be substituted with from 1 to 3 substituents selected from a methyl group, an ethyl group, a propyl group, a butyl group, a benzyl group, a phenyl group and a cyclohexyl group.
2. The adhesive of claim 1, wherein said primer is a copper salt.
3. The adhesive of claim 1, wherein said primer is an iron or cobalt salt.
4. The adhesive of claim 1, 2 or 3, wherein said primer further comprises water or a mixture of water and a water-miscible organic solvent.
5. The adhesive of claim 1, 2 or 3, wherein said water-miscible monomer is 2-hydroxyethylmethacrylate, present in a concentration of from 1 to 50% by weight of said primer.
6. The adhesive of claim 1, wherein said curing composition further comprises a co-initiator selected from the group consisting of cupric chloride, ferric chloride, cobalt chloride, camphor quinone, triethylamine hydrochloride, propylamine hydrochloride, butylamine hydrochloride, triethylbenzylammonium chloride, methacryloylcholine hydrochloride, a peroxide, a sulfinic acid salt and mixtures thereof.

* * * * *